United States Patent [19]

Brima

[11] 4,356,310

[45] Oct. 26, 1982

[54] PROCESS FOR PREPARING GAMMA-BUTYROLACTONE AND BUTENOLIDE

[75] Inventor: Thomas S. Brima, Cincinnati, Ohio

[73] Assignee: National Distillers & Chemical Corp., New York, N.Y.

[21] Appl. No.: 280,168

[22] Filed: Jul. 2, 1981

[51] Int. Cl.$^3$ .................. C07D 307/58; C07D 307/32
[52] U.S. Cl. .................................................. 549/295
[58] Field of Search ...................... 260/343.6, 346.75; 562/546

[56] References Cited

U.S. PATENT DOCUMENTS 3,325,516 6/1967 Fettis et al. ..................... 562/546
3,867,412 2/1975 Barker ............................ 260/346.75

FOREIGN PATENT DOCUMENTS 1157117 7/1969 United Kingdom ........... 260/346.75

Primary Examiner—Norma S. Milestone
Attorney, Agent, or Firm—Kenneth D. Tremain

[57] ABSTRACT

A mixture of gamma-butyrolactone and butenolide is obtained by reacting 1,3-butadiene with oxygen in the vapor phase at elevated temperature in the presence of a catalytically effective amount of a mixed metal oxide containing boron, molybdenum and titanium values.

9 Claims, No Drawings

PROCESS FOR PREPARING GAMMA-BUTYROLACTONE AND BUTENOLIDE

BACKGROUND OF THE INVENTION

1. Field of the Invention

This invention relates to processes for preparing lactones and, in particular, to processes for preparing gamma-butyrolactone and its unsaturated analogue, butenolide (gamma-crotonolactone), via the catalyzed vapor phase reaction of 1,3-butadiene and oxygen.

2. Description of the Prior Art

Both gamma-butyrolactone and butenolide are industrially important chemicals, the former finding use as a starting material for the production of 1,4-butanediol and butyric and succinic acids, as a solvent for resins, in the formulation of paint removers and in petroleum processing, and the latter, when hydrogenated in a known and conventional manner, providing gamma-butyrolactone.

A variety of procedures for the preparation of gamma-butyrolactone and butenolide are known. U.S. Pat. No. 2,636,898 to Buckley describes the oxidation of monoolefins and acetylenic compounds with nitrous oxide (which dissociates into oxygen and nitrogen at about 600° C.) to provide a variety of organic reaction products, e.g., the oxidation of 4-hydroxy-1-butyne to provide gamma-butyrolactone. U.S. Pat. No. 3,061,614 to Sweeney, et al. describes the catalytic carbonylation of allyl alcohol to provide gamma-butyrolactone. U.S. Pat. Nos. 3,065,243 to Dunlop, et al. and 3,113,138 to Franko-Filipasic, et al. each describes the preparation of gamma-butyrolactone by the catalytic hydrogenation of succinic anhydride.

U.S. Pat. No. 3,458,532 to Hayden relates to the preparation of unsaturated lactones by the reaction of ethylene or propylene with carbon monoxide in the presence of a catalyst containing the palladium salt of a strong acid. U.S. Pat. No. 4,119,642 to Larock describes the preparation of butenolides by the carbonylation of vinylmercurials. U.S. Pat. No. 4,175,089 to Heiba, et al. describes a process for preparing gamma-butyrolactones in which an olefin such as 1,3-butadiene is reacted with a carboxylate compound in the presence of an ion of manganese, cerium or vanadium.

SUMMARY OF THE INVENTION

It has now been discovered that mixtures of gamma-butyrolactone and butenolide, which can be resolved into their individual components employing conventional procedures or subjected to hydrogenation to convert the butenolide component to gamma-butyrolactone, are readily and conveniently prepared by the vapor phase reaction of 1,3-butadiene with oxygen in the presence of a catalytically effective amount of a substantially water-insoluble mixed metal oxide catalyst containing the metallic elements boron, molybdenum and titanium.

The term "mixed metal oxide" as used herein is to be understood in its art-recognized sense, i.e., as a combination of individual metal oxides which are more intimately associated with each other than the individual metal oxides of a mere mechanical mixture (viz. U.S. Pat. No. 2,769,847 to Robinson).

DESCRIPTION OF THE PREFERRED EMBODIMENTS

The starting 1,3-butadiene herein can be substantially pure but, more usually, will be of industrial or commercial quality, i.e., in admixture with minor amounts of one or more impurities.

The source of oxygen herein is not critical and includes pure oxygen, enriched air and atmospheric air, the latter being preferred for reasons of economy and convenience. By way of promoting conversion of 1,3-butadiene to gamma-butyrolactone and butenolide, it is advantageous to use a large stoichiometric excess of oxygen, e.g., from about 1.5 to 5 times the theoretical amount needed, care, of course, being observed not to provide an explosive mixture.

The reaction herein most readily occurs in the vapor phase and at elevated temperatures. Pressures of up to 5,000 psig and preferably, pressures ranging from atmospheric to 1,000 psig, can be used with good results. Temperatures can be widely varied and in general will be in the range of from about 100° C. to about 500° C., and preferably, from about 200° C. to about 400° C.

The reaction can be carried out on a batch or continuous basis, the latter being more readily suitable to lost-cost operation. The process herein contemplates the use of known and conventional oxidation-resistant apparatus which is commercially available from numerous sources.

The mixed metal oxide catalyst herein must contain boron, molybdenum and titanium values and optionally can be supported upon an inert inorganic carrier such as silica, silica gel, titania, zirconia, alumina, and the like. The atomic ratios of boron, molybdenum and titanium are advantageously selected to be within the respective ranges of 1:1:1–1:4:6.

The amount of catalyst employed can vary over fairly wide limits and the level of catalyst selected will be such as to provide a suitable range of superficial contact time, e.g., from a few seconds to a few minutes or more, under the prevailing reaction conditions. The relationship between superficial contact time, catalyst volume and reaction conditions is given by the equation:

$$\text{Superficial Contact Time} = \frac{\text{Volume Catalyst}}{\text{Total Vol. feed gases} \times \frac{T_1}{T_2} \times \frac{P_1}{P_2}}$$

Thus, for example, given a catalyst volume of 50 ml, a total feed gas volume of 179 ml/min (140 ml/min air and 39 ml/min 1,3-butadiene), $T_1$ = reaction temp. (Å) = 273 + 250 = 523 Å, $T_2$ = ambient temp. = 25 + 273 = 298 Å (temp. at which flow rate is measured) and pressure $P_1$ = pressure $P_2$ (reaction pressure = atmospheric = pressure at which the flow rate is measured), the superficial contact time is 9.55 seconds.

The process by which the mixed metal oxide catalyst is prepared appears to be critical since molybdena ($MoO_3$) on titania ($TiO_2$) treated with boric acid ($H_3BO_3$) when used for the oxidation of 1,3-butadiene did not provide a lactone. To provide a suitably active mixed metal oxide catalyst, a titanium halide such as titanium tetrachloride is reacted with boric acid or an alkyl borate to provide a titanium borate which is thereafter reacted with ammonium heptamolybdate to provide a solid which, after being optionally deposited upon a carrier such as any of these aforementioned, is calcined, preferably in a inert or oxygen-containing atmosphere and preferably below about 500° C., to yield the desired catalyst.

To demonstrate the unexpected activity of the catalyst herein for oxidizing 1,3-butadiene to a mixture of gamma-butyrolactone and butenolide, said catalyst was compared with several other metal oxide compositions. In the following examples, Example 1 illustrates the preparation of a boron titanium-molybdenum mixed metal oxide catalyst in accordance with this invention and Examples 2 to 5 illustrate the preparation of other metal oxide compositions.

EXAMPLE 1

B/Ti/Mo Mixed Metal Oxide

To a well-stirred suspension of boric acid (110 g, 1.78 m) in toluene (150 ml) was added titanium tetrachloride (133 ml, 230 g, 1.21 m) at room temperature. Stirring was continued until hydrochloric acid evolution was negligible (16 hours). The titanium borate formed was removed by filtration and dried in vacuo. The yield of 206 g indicated that not all of the chlorine had been eliminated.

A mixture of this titanium borate (43 g) and ammonium heptamolybdate (16.25 g, 0.013 m) (0.092 g atoms Mo) was ground to a fine powder and refluxed in absolute ethanol (50 ml). The suspension turned green after 45 minutes and blue on further refluxing (1½ hours). The solvent was then removed by evaporation, and the solid residue was dried at 110° C. for 2 hours. The green solid was then ground, blended with titania (50 g), pelletized and calcined at 400° C. for 16 hours. The finished catalyst contained 3.4% B, 51.1% Ti and 11.6% Mo as determined by atomic absorption.

EXAMPLE 2

B/V/Mo Metal Oxide

Vanadium trichloride (25 g, 0.15 m) dissolved in carbon tetrachloride was refluxed with boric acid (9.9 g, 0.16 m) in 100 mls toluene for 24 hours. All the vanadium borate so-formed was mixed with 7.0 g (0.0057 m) ammonium heptamolybdate and refluxed in methanol. The final catalyst was prepared as in Example 1.

EXAMPLE 3

B/Bi/Mo Metal Oxide

Bismuth molybdate (15 g) was ground with boric acid (30 g) and silica (120 g), extruded, dried and calcined at 400° C. for 4 hours.

EXAMPLE 4

B/Si/Mo Metal Oxide

To a solution of 100.8 g ammonium heptamolybdate in 1 liter water was added at room temperature 391.7 g 99% $SiCl_4$ over a period of 30 minutes with stirring. When the mixture became too thick to stir, 1 liter water was added. The resulting color of the mixture was green-yellow. The mixture was slowly evaporated to dryness under flowing air at 250° C. for 16 hours. To one half of the dry material was added 17.6 g boric acid in methanol. The mixture was dried and then calcined at 540° C. for 4 hours. Final weight of the powder was 103.3 g. The mixed oxide was used in this form.

EXAMPLES 5-8

Each of the foregoing metal oxide preparations were evaluated for 1,3-butadiene oxidation.

The oxidations were carried out in a 50 ml vapor-phase reactor separated by a perforated plate from a 75 ml preheater zone packed with chemically resistant glass beads. Gas feed rates were 39 mls/min (5.0 g/hr) 1,3-butadiene and 140 mls/min air. Screening runs were carried out in the temperature range 200° C.–350° C. From the reactor the effluents were first condensed and trapped using an ice-water bath, followed in sequence by an $O_2$ analyzer, gas-sampling bulb, a trap bathed in dry ice-acetone mixture and finally a wet-test meter. The condensate in the first trap was analyzed by gas chromatography [Column-Carbowax 20 M (8'×⅛")] at 160° C. and a flow rate of 75 mls/min $N_2$. The unconverted butadiene in the second trap was determined by direct weighing. Carbon oxides and other gases were determined by chromatography and measurement of total gas volume.

The results of the foregoing oxidations are set forth below as follows:

TABLE 1

1,3-BUTADIENE OXIDATIONS OVER VARIOUS METAL OXIDES

| Example | Catalyst Composition | Reaction Temp, °C. | Butadiene Conv, % | Selectivities % | |
|---|---|---|---|---|---|
| | | | | Butenolide | Gamma Butyrolactone |
| 5 | B/Ti/Mo (Ex. 1) | 250 | 53 | 22.0 | 2.0 |
| 6 | B/V/Mo (Ex. 2) | 250 | 50 | 6.6 | 1.0 |
| 7 | B/Bi/Mo (Ex. 3) | 290 | 80 | 4.2 | 0.2 |
| 8 | B/Si/Mo (Ex. 4) | 335 | 37 | low | — |

As these data show, the use of the catalyst according to the present invention (B/Ti/Mo mixed metal oxide of Example 1) to oxidize 1,3-butadiene produced much higher selectivities for the desired products, butenolide and gamma-butyrolactone (Example 5) than any of the other metal oxide compositions (Examples 6–8).

What is claimed is:

1. A process for preparing a mixture of gamma-butyrolactone and butenolide which comprises reacting 1,3-butadiene with oxygen in the vapor phase at elevated temperature in the presence of a catalytically effective amount of a mixed metal oxide catalyst containing boron, molybdenum and titanium values said mixed metal oxide catalyst being obtained by:
   (a) reacting a titanium halide with boric acid;
   (b) reacting the titanium and boron-containing reaction product of step (a) with ammonium heptamolybdate to provide a titanium, boron and molybdenum-containing solid; and,
   (c) calcining the solid obtained in step (b) to provide said catalyst.

2. The process of claim 1 wherein atmospheric air is the source of oxygen.

3. The process of claim 1 conducted at atmospheric pressure to 5,000 psig.

4. The process of claim 1 conducted at from about 100° C. to about 500° C.

5. The process of claim 1 conducted at from about 200° C. to about 400° C.

6. The process of claim 1 wherein the catalyst is supported on an inert inorganic carrier.

7. The process of claim 1 wherein the catalyst is supported on silica or titania.

8. The process of claim 1 wherein the catalyst possesses a gram atom ratio of boron to molybdenum to titanium of from about 1:1:1 to about 1:4:6.

9. The process of claim 1 wherein calcining is conducted at a temperature below about 500° C.

* * * * *